(12) United States Patent
Roberts

(10) Patent No.: US 10,494,774 B2
(45) Date of Patent: Dec. 3, 2019

(54) ASPHALT DIELECTRIC MEASUREMENT ACCURACY IMPROVEMENT USING ASPHALT SURFACE TEMPERATURE

(71) Applicant: Geophysical Survey Systems, Inc., Nashua, NH (US)

(72) Inventor: Roger Roberts, Amesbury, NH (US)

(73) Assignee: GEOPHYSICAL SURVEY SYSTEMS, INC., Nashua, NH (US)

(*) Notice: Subject to any disclaimer, the term of this patent is extended or adjusted under 35 U.S.C. 154(b) by 34 days.

(21) Appl. No.: 16/008,560

(22) Filed: Jun. 14, 2018

(65) Prior Publication Data

US 2019/0301109 A1    Oct. 3, 2019

Related U.S. Application Data

(60) Provisional application No. 62/650,037, filed on Mar. 29, 2018.

(51) Int. Cl.
*E01C 19/28* (2006.01)
*G01N 33/42* (2006.01)
(Continued)

(52) U.S. Cl.
CPC ......... *E01C 19/288* (2013.01); *G01N 33/383* (2013.01); *G01N 33/42* (2013.01); *G01S 13/885* (2013.01)

(58) Field of Classification Search
CPC ..... E01C 19/288; G01N 33/383; G01N 33/42
See application file for complete search history.

(56) References Cited

U.S. PATENT DOCUMENTS 5,900,736 A * 5/1999 Sovik ............... G01N 9/24
324/663
5,952,561 A * 9/1999 Jaselskis ............ E01C 19/288
73/78
(Continued)

FOREIGN PATENT DOCUMENTS

EP    1795885 A1    10/2011

OTHER PUBLICATIONS

WikiHow, Flow to Make Silage: 12 Steps (with Pictures), [date accessed Dec. 21, 2017]: https://www.wikihow.com/Make-Silage.
(Continued)

*Primary Examiner* — Abigail A Risic
(74) *Attorney, Agent, or Firm* — Michael J. Feigin, Esq.; Feigin and Fridman LLC

(57) ABSTRACT

Dielectric values of cooling asphalt are obtained despite the presence of water on the surface thereof which effects the measured dielectric. The temperature of the surface of the asphalt is measured simultaneous or contemporaneous to a measurement of the dielectric, the former by way of an infrared camera and the latter by way of a ground penetrating radar transceiver, in embodiments of the disclosed technology. The ground penetrating radar moves with a roller on the surface of the asphalt and the camera can also move with and be mounted on the housing or can be separate, such as in a drone flying at a higher altitude than the asphalt and housing. Using a reference measurement for the mix design of the asphalt without water or with varying degrees of water, the changed dielectric due to the presence of water can be corrected to reveal the dielectric of the asphalt alone.

20 Claims, 6 Drawing Sheets

(51) Int. Cl.
*G01N 33/38* (2006.01)
*G01S 13/88* (2006.01)

(56) References Cited

U.S. PATENT DOCUMENTS

| | | | | |
|---|---|---|---|---|
| 6,414,497 | B1* | 7/2002 | Sovik | G01N 9/00 324/663 |
| 7,239,150 | B2* | 7/2007 | Troxler | G01N 22/00 324/634 |
| 10,145,837 | B2* | 12/2018 | Troxler | G01S 13/0209 |
| 2002/0057095 | A1* | 5/2002 | Zoughi | G01N 22/00 324/646 |
| 2002/0175691 | A1* | 11/2002 | Sovik | G01N 9/00 324/654 |
| 2005/0150278 | A1* | 7/2005 | Troxler | G01N 22/00 73/78 |
| 2012/0027513 | A1* | 2/2012 | Wang | C04B 26/26 404/77 |
| 2015/0268218 | A1* | 9/2015 | Troxler | G01S 13/0209 342/21 |

OTHER PUBLICATIONS

In-Place Hot Mix Asphalt Density Estimation Using Ground Penetrating Radar, Imad I. Al-Qadi et al., Center of Excellence for Airport Technology and University of Illinois at Urbana-Champaign Advanced Transportation Research and Engineering Laboratory (ATREL), ICT Report No. 11-096, Dec. 2011 [date accessed Mar. 23, 2018].

Hoffmann, Thomas et al., "Radiometric density measurement for silage compaction in bunker silos." Agric Eng Int: CIGR Journal, Sep. 2013, vol. 15, No. 3, p. 191-197, [date accessed Dec. 21, 2017]: open access at http://www.cigrjournal.org.

* cited by examiner

ASPHALT DIELECTRIC MEASUREMENT ACCURACY IMPROVEMENT USING ASPHALT SURFACE TEMPERATURE

FIELD OF THE DISCLOSED TECHNOLOGY

The present technology relates to the calculation of the dielectric of asphalt pavement. More particularly, the present technology relates to a method to make the dielectric measurements more accurate and, in some embodiments, in real-time.

BACKGROUND OF THE DISCLOSED TECHNOLOGY

GPR, or ground-penetrating RADAR (where RADAR is "RAdio Detection And Ranging), is a technology used to assess the composition and location of heterogeneous materials. GPR uses radio frequencies and is particularly useful in that it is both non-destructive and non-ionizing. In fact, GPR uses frequencies similar to a cellular phone, but at far lower power levels. Common applications include locating the precise position of rebar within a concrete wall/floor, identifying and locating buried objects underground, assessing the quality and uniformity of an asphalt or concrete highway surface, and detecting deterioration on bridge decks. In road surface applications, GPR is used, for example, to detect cracks, fissures, or contamination in any one of the chip seal, pavement layers, gravel base, and so forth. In many roadway applications, a resolution of features of the road surface of less than one inch (2.54 cm) is desired. Such systems may be mounted on vehicles traveling over the surface while acquiring measurement data.

Referring now specifically to paving of asphalt surfaces (a mixture of bitumen pitch with sand, gravel, or stone), when asphalt surfaces are built or rehabilitated, the degree of compaction of the newly-laid asphalt is very important. Poorly-compacted asphalt has a lifetime that may be as little as half the lifetime of properly compacted asphalt. Asphalt compaction levels are often measured after the asphalt compaction process is completed to reward or penalize the paving contractor depending on the measured compaction levels. The measurements may be made with ground penetrating radar (GPR) or handheld nuclear or non-nuclear gauges. Jaselskis et al, (U.S. Pat. No. 5,952,561) provide ample discussion on the compaction process and methods comprising the current state-of-the art.

Ground penetrating radar has the potential of being used on the rollers that do the compacting to provide real-time feedback to the roller operator so that the roller operator can determine how many passes with the roller are necessary for optimum compaction. A GPR system that produces real-time dielectric values has been developed and is used to for quality assurance of asphalt roads after they have been compacted. This system can be calibrated based on the asphalt mix used for a particular paving project to output the asphalt density or percent void content in real-time. One issue that limits the accuracy of the GPR measurements, and consequently its deployment on rollers, is the presence of wetness on the asphalt surface. The source of the wetness might be precipitation or the fine spray that soaks the surface of the rollers to prevent the asphalt from sticking to the roller as it is rolling over the hot asphalt. The GPR method uses the amplitude of the reflection of the RADAR waves from the asphalt surface to calculate the asphalt dielectric. The presence of water on the asphalt surface impacts the surface reflection resulting in inaccurate and often non-useful measurements.

Thus, there is a need to be able to determine compaction of the asphalt despite the inaccurate measurements that result from water on the surface thereof.

SUMMARY OF THE DISCLOSED TECHNOLOGY

Therefore, the new method provides the necessary information in order to apply a correction factor to the measured dielectric calculated from the GPR, which in turn, is related to the amount of compaction of the asphalt. There is a direct correlation between the measured dielectric and the compaction level allowing one who has an accurate measurement of the dielectric to determine the compaction of the asphalt.

Embodiments of the disclosed technology correct for dielectric measurements of asphalt which otherwise returns erroneous values due to the presence of water on part or all of the surface of the asphalt. This is accomplished by compacting a length and/or width of asphalt with a roller moving across the length and/or width. While the roller is moving and the asphalt is being compacted, a temperature of the asphalt is measured with a temperature measuring device such as an infrared camera, wire comb, or the like. Further, while the roller is moving a radar device (a device which transmits pulses of high-frequency electromagnetic waves that are reflected off an object, in this case, asphalt, back to the source) transmits wide-band or ultra wide-band frequency range pulses into the asphalt measures the received response. A dielectric, or measure of conductivity, for the asphalt is determined based on the received response. A change in dielectric at a portion of the length (or width) being compacted which corresponds further to detection of a lower temperature is detected or determined. Based on this detection or determination, the dielectric is adjusted to compensate therefor.

The recently laid asphalt (e.g. same day or within the same hour or period of four hours or less) is typically at a temperature well above that of the boiling point of water, such as at 200 or 300 degrees Celsius. Water, if on the surface and not yet evaporated, is at a maximum of 100 degrees Celsius. Thus, a change in measured dielectric for a portion of said length corresponding to a lower temperature measured or determined during the measuring of the temperature can be assumed, in some embodiments of the disclosure technology, due to the presence of water. The measured dielectric is then adjusted accordingly, to remove the effect of the water based on one or more of a known dielectric or amount dielectric change caused by the water and/or percentage of water covering an area within a received response from the radar device. The radar device might, for example, measure an area of about 6 inches or 15 centimeters, whereas temperature sensing can be, for example, less than every 0.5 inches or 1 centimeter or less. The radar can then be said to have more granular measurements than the temperature sensing which has more fine measurements. Thus, a percentage coverage of the area with water can be determined accordingly, in order to calculate the effect on the dielectric returned and compensate therefor. The above can be done in real-time while rolling the roller across the asphalt or as part of pre- or post-processing, such as by finding a dielectric for a particular mix design and the particular mix design with varying percentages of water there-on the surface.

The temperature sensing can be carried out using a visual sensor such as an infrared camera or sensor which is mounted on the housing of a device conducting (carrying out) the compacting. A wire comb brush with temperature measuring capabilities can also or instead be used. Further, a radar transmitter conducting the transmitting can be mounted on the housing with a distance between a measuring end of the radar transmitter and the visual sensor (also, in such an embodiment mounted on the housing) known. Measuring of the temperature and measuring the dielectric over a particular location on the asphalt can then be contemporaneous, but not always or not necessarily simultaneous (in this particular embodiment) because they each pass over a particular point on the asphalt at a different time. For purposes of this disclosure, "simultaneous" is defined as "within 1 second" (in the same inertial reference frame) and "contemporaneous" is defined as within 5, 10, 30, or 60 minutes. Based on a speed of movement of the roller as the roller (and the housing connected-thereto) is moving across the length and based on the distance between the measuring end of the radar transmitter and the visual sensor, the varying measurements are correlated to find the dielectric, modify the dielectric (if necessary), and measure the temperature over the same point or location. A "point" is a theoretical or smallest measurable point with the equipment used whereas a location is, for purposes of this disclosure, defined as within six inches (about 15 centimeters) of accuracy on the surface of the asphalt.

The visual sensor can also be mounted on drone above the asphalt, and at times, being above the roller (where "about the roller" is defined as "having a view of the roller and being at a higher altitude than the roller"). The temperature of a surface beneath the roller is measured by the camera contemporaneous and non-simultaneous to the transmitting of the wide-band radar (directly) beneath the roller in some embodiments or at some times when embodiments of the disclosed technology are carried out.

The detecting of a change in measured dielectric is compared to a reference measurement for a mix design in some embodiments. The reference measurement of the mix design can be determined by measuring a dry portion of the mix design (sample of the asphalt laid or to be laid) and also be determined based on finding a changed dielectric along a length of asphalt, e.g. where the dielectric drops but then returns to it's previous value along the length. By determining the amount of water where the dielectric and temperature dropped, one can find other locations or portions of lengths of asphalt where the water percentage coverage was substantially equal thereto, and use this to adjust the dielectric substantially the same amount or percentage.

The above methods can be carried out with devices including a compacting roller (roller which passes over the surface of asphalt). Asphalt, for purposes of this disclosure, is any material used to cover a surface which, when covering the surface, is at temperature other than that of water placed on it's surface, such as at a temperature above 100 degrees Celsius. A temperature measuring device is used to measure the temperature of the asphalt and/or water on the asphalt and can be a thermometer, an infrared sensor/camera, or a wand or probe, or any combination thereof. A wide-band radar transceiver is attached to the housing, the housing being a device which is connected to the roller and moves laterally across the asphalt with the roller. The transceiver is in a fixed position relative to the lateral movement of the roller (while the roller rolls circumferentially along the asphalt). Embodiments can also be carried out without a roller or wheel so long as the transceiver moves along the surface and measures a received radio response which is compared to temperature. In any of these cases, a processor can be used to determine a drop in temperature received and take a measured dielectric (which is determined based on the received response from the transceiver) to adjust the dielectric measurement based on the drop in temperature, the drop in temperature assumed or determined ("determined" being a more accurate version of "assuming", based on known or more data versus based on a most probable cause, based on past evidence or events) due to the presence of water on the surface of asphalt.

A system, such as one carrying out what is described above, can measure a substantially equal dielectric and temperature at a first and third area corresponding substantially to the dielectric of the reference measurement. However, a different dielectric and a lower temperature at a second area between said first and third point might be measured where further a certain percentage of water is determined to cover the second area. The measured dielectric of a fourth area of the asphalt which is non-overlapping with the first, second, and third areas and has a substantially equal percentage of water to the second area, is adjusted an amount substantially equal to a difference in the measured dielectric of the second area compared to the first and third area.

Any device or step to a method described in this disclosure can comprise, or consist of, that which it is a part of, or the parts which make up the device or step. The term "and/or" is inclusive of the items which it joins linguistically, and each item by itself.

DETAILED DESCRIPTION OF EMBODIMENTS OF THE DISCLOSED TECHNOLOGY

Figure 1:
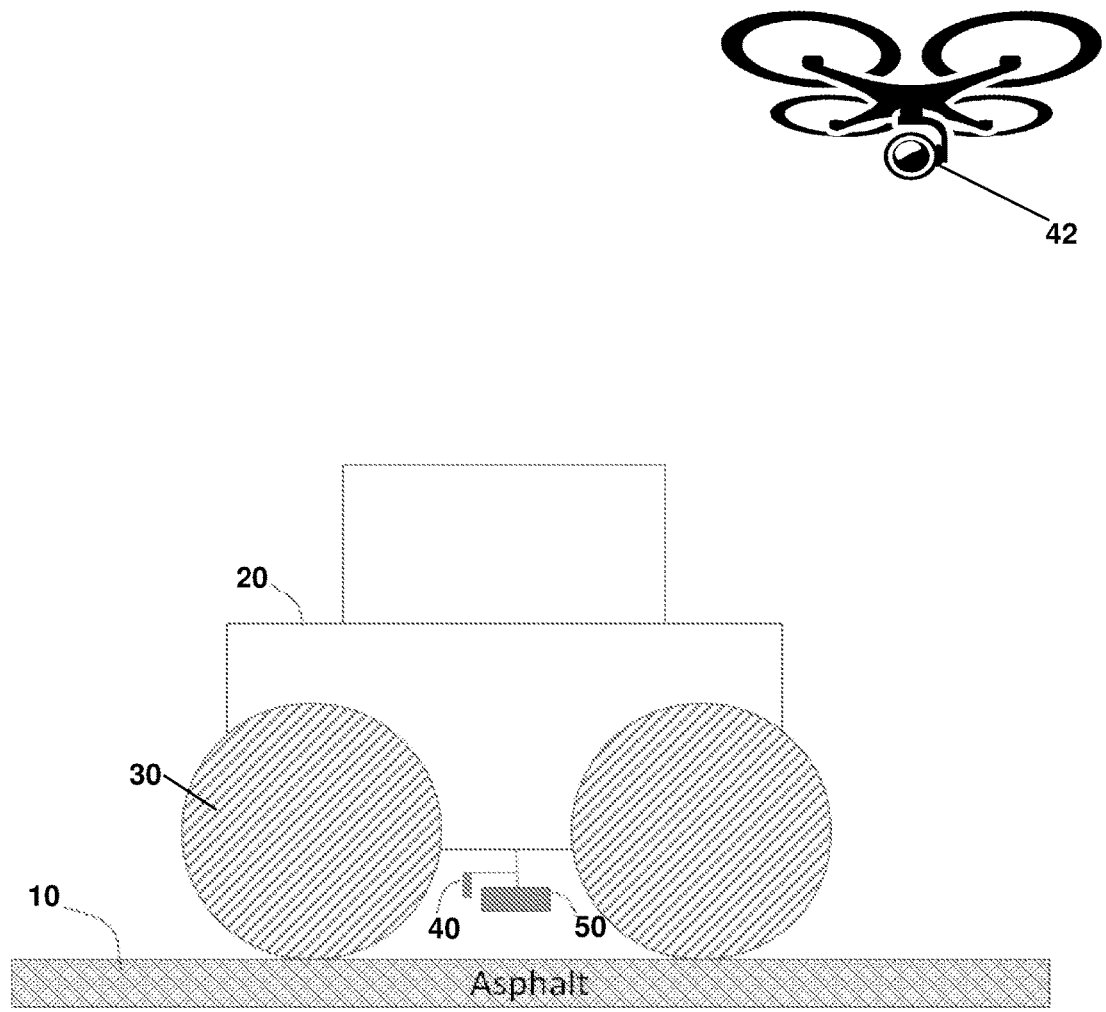
FIG. 1 shows a system with a GPR antenna and an infrared temperature sensor mounted on a roller in an embodiment of the disclosed technology.

A method for correcting and/or filtering dielectric values calculated from GPR over asphalt during the compaction process is disclosed herein. A temperature sensor is mounted in close proximity (but separated from) a ground penetrating radar (GPR) antenna. The temperature is recorded at the same location as the GPR measurements and based on the temperature and the amount of local temperature contrast, the presence of surface water can be detected and subsequently the dielectric measurements at the locations with surface water can then be corrected or filtered.

The typically large temperature gradient between the asphalt (currently being compacted) and the ambient temperature means that water landing on the asphalt locally cools the hotter asphalt surface. Areas with a greater amount of water are cooled via evaporation to a greater degree. The presence of water can therefore be detected by its thermal anomaly, assuming the asphalt is laid down at temperatures that are either locally homogeneous or, at least, where the temperature of the water is cooler than the surface of the asphalt being measured in general. This is the principle behind using another instrument to measure the temperature of the asphalt in real-time at the same location as the GPR measurement and make any corrections to the calculated dielectric based on the temperature of the asphalt and the local areal temperature contrast at the measurement location.

Asphalt has a particular mix design with a particular obtainable dielectric for each mix design. A particular mix design is defined as one which is a substantially (at least 90% so) homogenized mixture of rock, bitumen, fibers, or other materials used to produce asphalt or another surface covering material. This asphalt can also have air voids therein. With a sample of asphalt, a dielectric can be obtained and when paving, one can measure the dielectric in real-time but in the disclosed technology, compensates for surface water having an effect on the measured dielectric in order to obtain a more accurate result as part of post-processing or in real-time (as fast as the equipment used to measure temperature and dielectric can provide readings and the data can be processed, or, alternatively, within 1, 5, 30, or 60 seconds).

The presence of surface water affects the measured dielectric of asphalt obtained from non-contact GPR antennas. This presents a problem to the application of GPR antennas mounted on rollers because rollers are wetted (having water or other liquid applied thereto) to prevent the asphalt mix from sticking to their surface. The present invention incorporates the detection of localized wet areas using temperature sensors to adjust or filter out the corresponding dielectric values, thereby negating the impact of surface moisture and making GPR on a roller a viable application for measuring asphalt compaction.

While an infrared sensor is disclosed to determine water content, any visual or other sensor which can detect surface moisture and, in some cases, the extent thereof, may be used. When infrared is used, one sees an obvious difference where water is present as water has a maximum temperature of 100 C, but asphalt being laid is typically much higher. In some embodiments, the GPR (ground penetrating radar) device is measuring about a 6 inch diameter and averaging the dielectric value over this area. The antenna used for the GPR device is, in some embodiments and not by limitation, from 1 to 10 GHz and up and in others between 2 and 5 GHz or between 5 and 6 GHz inclusive. The dipole length can be about 5 centimeters. Once the calibration curve or series of curves is known for the particular mix design, this can be used as reference so that when the asphalt is being laid down the variable left to discover is void content (the amount of air in the asphalt compared to the reference mix design, or, in other embodiments, the variation in compaction or percent compaction).

Embodiments of the disclosed technology will become clearer in view of the following description of the figures.

FIG. 1 shows a system with a GPR antenna and an infrared temperature sensor mounted on a roller in an embodiment of the disclosed technology. A housing 20 is connected to at least one roller 30. The roller passes over the asphalt 10, compacting the asphalt in embodiments of the disclosed technology. While doing so, GPR measurements are taken with a transceiver 50 transmitting and receiving pulses in a wide-band or ultra wide-band range. A temperature sensor determines the temperature of the asphalt contemporaneous or simultaneous to the compacting and/or GPR measuring. This temperature sensor can be taken via a camera 40 or 42, such as one with an infrared sensor where the temperature is determined based on infrared received to the camera. The camera can be a drone-mounted camera 42 which determines temperature of the asphalt from above the housing 20 connected to the roller(s) 30. In such a case, the camera 42 will receive the heat information about the asphalt just before or after the compaction as the housing can block a view of the asphalt. In such cases, the measurements and/or data received by the GPR and camera 42 are contemporaneous in embodiments of the disclosed technology. The camera 40 is, in embodiments, mounted to and moves with the housing 20 as well as the (lateral) movement of the roller 30.

Figure 2:
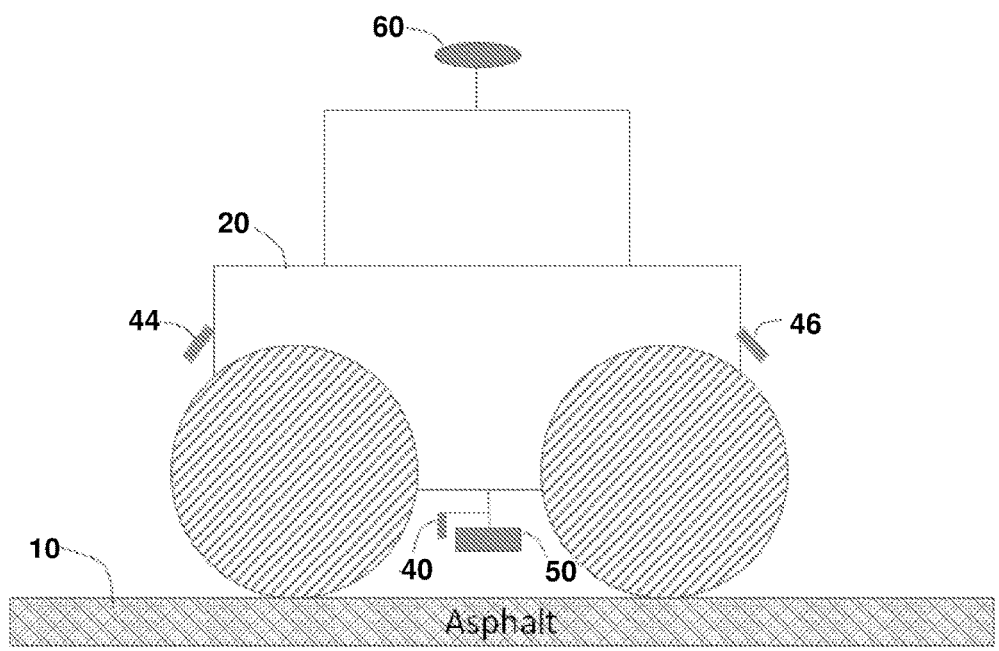
FIG. 2 shows another version of a system as shown in FIG. 1 with additional or different temperature sensors which are used in embodiments of the disclosed technology.

FIG. 2 shows another version of a system as shown in FIG. 1 with additional or different temperature sensors which are used in embodiments of the disclosed technology. In this embodiment, cameras 44 and/or 46 are used to measure the temperature of the asphalt just before and/or after compaction by a roller 30. The temperatures measured by a front camera 44 and rear camera 46 can be averaged when used to determine the presence of water. Again, it should be understood that recently laid asphalt generally has a temperature well in excess (greater than 50 or 100 degrees Celsius) of the boiling point of water, so non-evaporated water will be detectable based on a temperature of 100 degrees or less as detected by a thermometer (wire probe or comb) or infrared camera 40, 42, 44, or 46. This detection of water at a position where a GPR transceiver 50 is sending/receiving data can be used to correct a determined dielectric for a particular location or point measured by GPR based on a known or determined error caused by a particular percentage or full coverage of water over the particular location or point.

Figure 3:
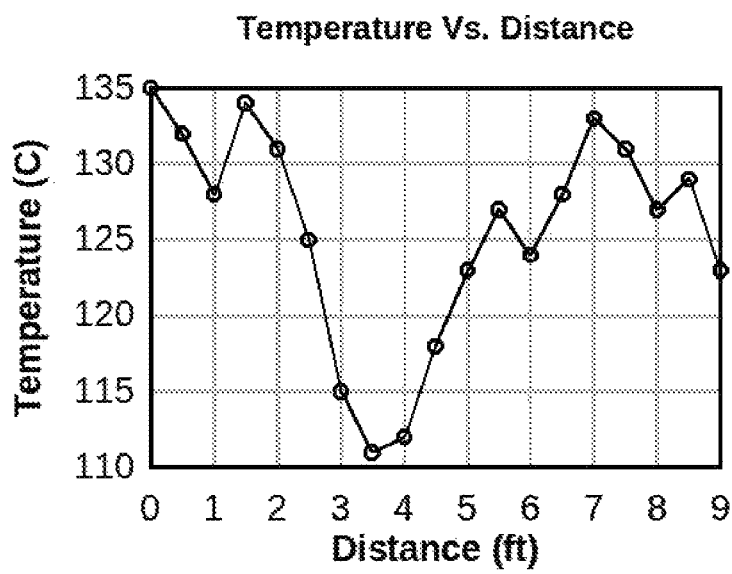
FIG. 3 shows a graph of the temperature measured along a path in an example of carrying out embodiments of the disclosed technology.

FIG. 3 shows a graph of the temperature measured along a path in an example of carrying out embodiments of the disclosed technology. A significant drop in measured temperature is observed, in this example, between 2.5 and 4 feet (ft) in distance. One implementation of the disclosed technology associates the excessive temperature drop near to or below 100 degrees Celsius to surface wetness at this location from 2.5 to 4 feet and corrects same based on a determined percentage water coverage found via a temperature sensing mechanism and/or abrupt change in dielectric compared to nearby areas.

Figure 4:
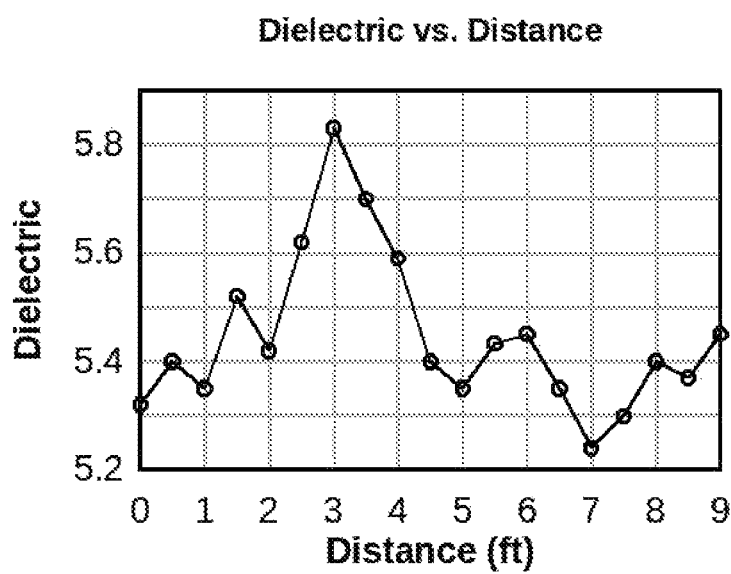
FIG. 4 is a graph of measured dielectric measured using a GPR system in an embodiment of the disclosed technology.

FIG. 4 is a graph of measured dielectric measured using a GPR system in an embodiment of the disclosed technology. One can again see in this example that the dielectric has risen from about 5.4 where there was no temperature drop to 5.6 and 5.8 from a distance of about 2 feet to 4.5 feet. Thus, when comparing the temperature to the dielectric from 2 feet to 4.5 feet, it becomes clear that the dielectric change is likely due to the presence of water rather than an actual change in the dielectric of the asphalt.

Figure 5:
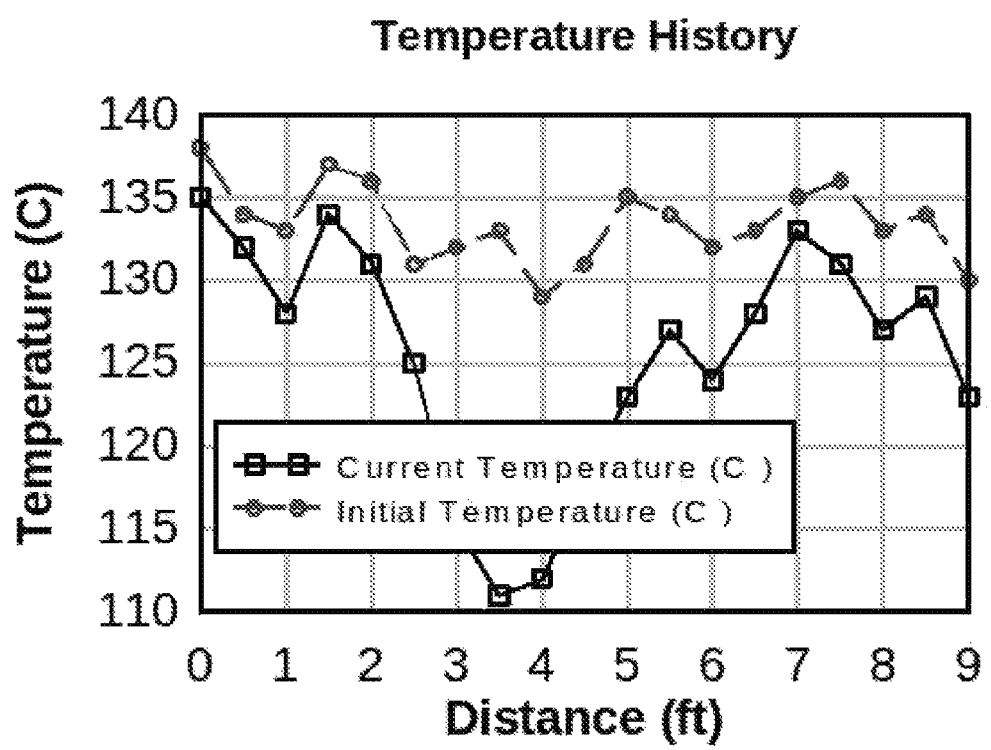
FIG. 5 is a graph of temperature history over a length of asphalt in each of multiple passes in an embodiment of the disclosed technology.

FIG. 5 is a graph of temperature history over a length of asphalt in each of multiple passes in an embodiment of the disclosed technology. Through subsequent passes one can find the temperature due the presence of water and lacking water and find a dielectric for each position and correct for, or confirm a correction made, due to the presence of water or moisture on the surface of the asphalt. There are multiple methods of determining the effect of water on the dielectric including finding the dielectric for the mix design before and/or after the compaction through taking a "puck" or core sample. When can use this as a reference point as well as create reference points with water by covering a surface measured by GPR with partial or full amounts of water and determining how the partial and/or full coverage of water on the surface changes the dielectric. Then, when measuring a location or point which has water on the surface, based on the temperature measurements of various points therein, one can determine the percentage coverage of water within the dielectric measurement and make an adjustment therefor. One method of carrying out same is described with reference to FIG. 6, below.

Figure 6:
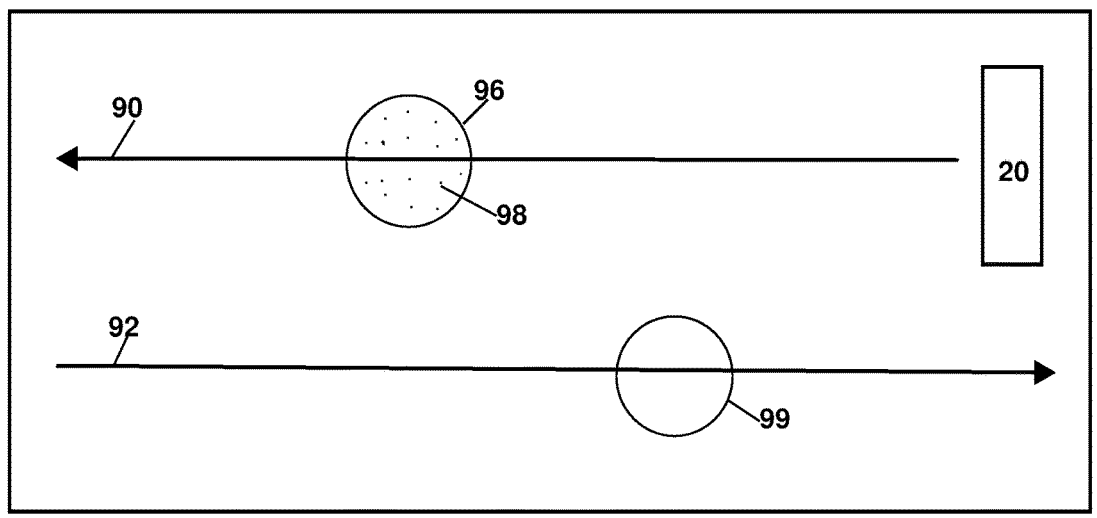
FIG. 6 is a plan view of asphalt showing a travel path of a roller with housing and associated devices in an embodiment of the disclosed technology.

FIG. 6 is a plan view of asphalt showing a travel path of a roller with housing and associated devices in an embodiment of the disclosed technology. Here, a housing 20 with a roller and ground penetrating radar transceiver moves in concept along path 90 and then along path 92. For purposes of this example, these are two different lateral paths covering locations and points along each lateral point. In this example, the circle 96 represents a measurement area of the ground penetrating radar transmission and received response at a moment in time. In some embodiments, the GPR (ground penetrating radar) device is measuring about a 6 inch diameter and averaging the dielectric value over this area. The antenna used for the GPR device is, in some embodiments and not by limitation, from 1 to 10 GHz and up and in others between 2 and 5 GHz or between 5 and 6 GHz inclusive. The dipole length can be about 5 centimeters. Once the calibration curve or series of curves is known for the particular mix design, this can be used as reference so that when the asphalt is being laid down the variable left to discover is void content (the amount of air in the asphalt compared to the reference mix design, or, in other embodiments, the variation in compaction or percent compaction).

Referring still to FIG. 6, within the measurement circle 96 of the GPR are multiple temperature measurement points 98 (the dots within the circle), by way of example. The temperature measured at each point can vary due to the presence of water at each point. Based on, in this example, about 16 measurement points water might be detected (due to a lower temperature) at 50% of the points representing a calculated average of 50% water coverage. The dielectric at this point might be determined to rise from 5.4 to 5.6 (by way of example only) with the 50% water coverage where as the 5.4 value or substantially equal thereto is found along the path 90 at locations/points both before and after the area with water coverage. Thus, the 5.4 can be determined to be a baseline for the mix design, or the mix design can be measured separately and/or with 50% water coverage to determine the 5.4 and 5.6 values. Then when passing along path 92 at circle 99, another circular of measurement point in time for the GPR, if 50% water is detected (based on lower temperature) then a dielectric of 5.6 can be found to be substantially like that of measurement point 96 and corrected to 54.

Figure 7:
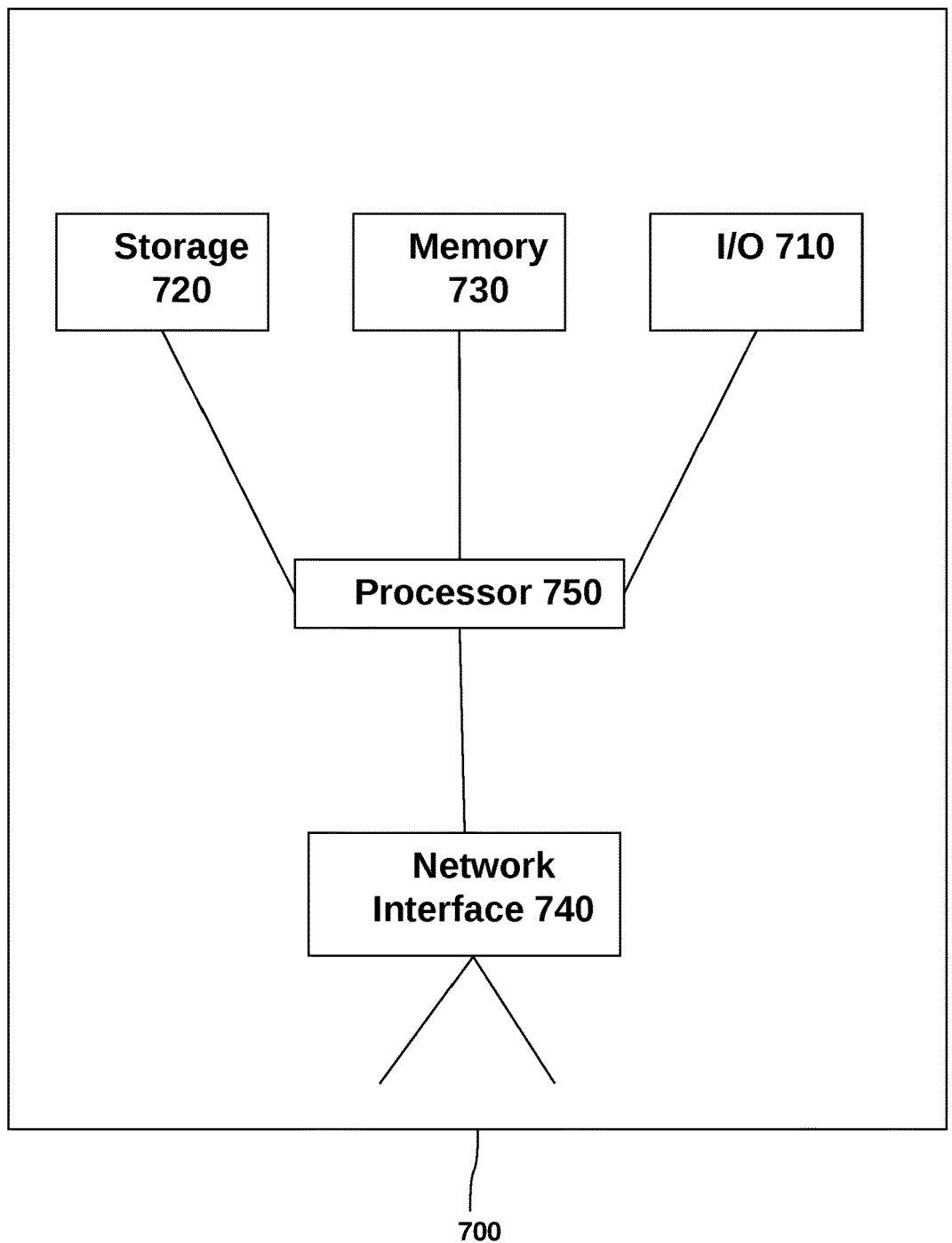
FIG. 7 shows a high-level block diagram of a device that may be used to carry out the disclosed technology.

FIG. 7 shows a high-level block diagram of a device that may be used to carry out the disclosed technology. Device 700 comprises a processor 750 that controls the overall operation of the computer by executing the measurement device's program instructions which define such operation. The measurement device's program instructions may be stored in a storage device 720 (e.g., magnetic disk, flash disk, database) and loaded into memory 730 when execution of the measurement device's program instructions is desired. Thus, the measurement device's operation will be defined by the measurement device's program instructions stored in memory 730 and/or storage 720, and the measurement device will be controlled by processor 750 executing the measurement device's program instructions. A device 700 also includes one or a plurality of input network interfaces for communicating with other devices via a network (e.g., the internet). A device 700 also includes one or more output network interfaces 710 for communicating with other devices. Device 700 also includes input/output 740 representing devices which allow for user interaction with the computer 700 (e.g., display, keyboard, mouse, speakers, buttons, etc.). One skilled in the art will recognize that an implementation of actual devices will contain other components as well, and that FIG. 7 is a high level representation of some of the components of such a measurement device for illustrative purposes. It should also be understood by one skilled in the art that the method and devices depicted in FIGS. 1 through 6 may be implemented on a device such as is shown in FIG. 7.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only illustrative and not restrictive. All changes that come within the meaning and range of equivalency of the claims are to be embraced within their scope. Combinations of any of the methods, systems, and devices described hereinabove are also contemplated and within the scope of the invention.

I claim:

1. A method of correcting dielectric measurements of hot asphalt, comprising the steps of:
   compacting a length of said asphalt with a roller moving across said length;
   contemporaneous to said compacting, measuring temperature of said length of said asphalt;
   while carrying out said moving, transmitting wide-band radar into said asphalt and measuring a received response;
   detecting a change in measured dielectric for a portion of said length corresponding to a lower temperature measured during said step of measuring of said temperature;
   adjusting a dielectric measurement value to compensate for said change in temperature.

2. The method of claim 1, wherein said adjusting is based on a presumption of detection of the presence of water.

3. The method of claim 2, wherein said wide-band radar measurement is more granular than said temperature measurements and a percentage water coverage per wide-band radar measurement is determined or estimated based on said measuring of temperature.

4. The method of claim 3, wherein a change in dielectric measurement due to presence of various percentages of water on said asphalt is determined in one of pre-processing or post-processsing, said change in said dielectric measurement used as a basis in said step of adjusting said dielectric to compensate for said change in temperature.

5. The method of claim 1, wherein a device used for said measuring temperature is a visual sensor.

6. The method of claim 5, wherein said visual sensor is an infrared sensor mounted on a housing of a device conducting said compacting.

7. The method of claim 6, wherein:
   a radar transmitter conducting said transmitting is mounted on said housing;

a distance between a measuring end of said radar transmitter and said visual sensor mounted on said housing is known; and said measuring of said temperature and said measuring said dielectric are corresponded to each other based on a speed of movement of said roller as said roller is moving across said length, further based on said distance between said measuring end of said radar transmitter and said visual sensor.

8. The method of claim 5, wherein said visual sensor is an infrared camera mounted on drone above said roller and temperature of a surface beneath said roller is measured with said camera contemporaneous and non-simultaneous to said transmitting of said wide-band radar beneath said roller.

9. The method of claim 1, wherein said detecting a change in measured said dielectric is compared to a reference measurement for a mix design.

10. The method of claim 9, wherein a change in measurement of said dielectric along said portion of said length between two other portions is between two positions of said asphalt which substantially match a dielectric of said reference measurement; and said change in measurement of said dielectric along said portion is used to compensate for a dielectric measurement of a future measured asphalt having substantially a same temperature change as said portion of said length.

11. A system for correcting dielectric measurements of hot asphalt, comprising:

a compacting roller attached to a housing and adapted to roll along a length of asphalt;

a temperature measuring device adapted to contemporaneously measure temperature of asphalt below said roller;

a wide-band radar transceiver attached to said housing such that said transceiver is in a fixed position relative to movement of said roller;

a processor determining a drop in temperature received from said temperature measuring;

wherein a dielectric of said asphalt used in further calculations and based on a received response from said transceiver is adjusted based on said determining of said drop in temperature.

12. The system of claim 11, wherein said drop in temperature is caused by water on a surface of said asphalt; and said measured dielectric is adjusted based on a percentage of water detected.

13. The system of claim 12, wherein said wide-band radar transceiver has a lesser resolution than said temperature measuring device; and a water coverage percentage used in said step of adjusting said measured dielectric is based on an average of multiple measurements of said temperature, each at a different point, within a single measurement made with said transceiver.

14. The system of claim 13, wherein said measured dielectric is adjusted in post processing, based on saved data with regards to presence of water on said surface of said asphalt.

15. The system of claim 11, where said temperature measuring device is a visual sensor.

16. The system of claim 15, wherein said visual sensor is an infrared sensor mounted on said housing.

17. The system of claim 16, wherein based on a known distance between a measuring end of said wide-band radar transceiver, said visual sensor, and a velocity of said roller a position of said asphalt are correlated when determining dielectric of said position measured at two different non-simultaneous but contemporaneous times by each of said wide-band radar transceiver and said temperature sensor.

18. The system of claim 15, wherein said visual sensor is an infrared camera mounted on a drone above said roller and temperature of a surface beneath said roller is measured with said camera contemporaneous and non-simultaneous to said transmitting of said wide-band radar beneath said roller.

19. The system of claim 11, wherein said received response from said transceiver is adjusted based on a dielectric of a reference measurement for a mix design of said asphalt.

20. The system of claim 19, wherein said system measures a substantially equal dielectric and temperature at a first and third area corresponding substantially to said dielectric of said reference measurement;

said system measures a different dielectric and a lower temperature at a second area between said first and third point;

a certain percentage of water is determined to cover said second area; and said measured dielectric of a fourth area of said asphalt which is non-overlapping with said first, second, and third areas and has a substantially equal percentage of water to said second area, is adjusted an amount substantially equal to a difference in said measured dielectric of said second area compared to said first and third area.

* * * * *